United States Patent
Ueno

(10) Patent No.: US 9,864,845 B2
(45) Date of Patent: Jan. 9, 2018

(54) SIMULATION METHOD FOR MACROMOLECULAR MATERIAL

(71) Applicant: SUMITOMO RUBBER INDUSTRIES, LTD., Kobe-shi, Hyogo (JP)

(72) Inventor: Shinichi Ueno, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 810 days.

(21) Appl. No.: 14/219,699

(22) Filed: Mar. 19, 2014

(65) Prior Publication Data

US 2014/0309971 A1 Oct. 16, 2014

(30) Foreign Application Priority Data

Apr. 15, 2013 (JP) ................. 2013-085077

(51) Int. Cl.
G06F 17/10 (2006.01)
G06F 19/00 (2011.01)
G06F 17/50 (2006.01)

(52) U.S. Cl.
CPC ........ G06F 19/701 (2013.01); G06F 17/5009 (2013.01); G06F 2217/16 (2013.01)

(58) Field of Classification Search
CPC . G06F 19/701; G06F 17/5009; G06F 2217/16
See application file for complete search history.

(56) References Cited

PUBLICATIONS

Vagelis A. Harmandaris et al., "Atomistic molecular dynamics simulation of stress relaxation upon cessation of steady-state uniaxial elongational flow," 2000, Macromolecules, vol. 33, pp. 8062-8076.*
V. A. Harmandaris et al., "Hierarchical modeling of polystyrene: from atomistic to coarse-grained simulations," 2006, Macromolecules, vol. 39, pp. 6708-6719.*
Jason D. Perlmutter et al., "All-Atom and coarse-grained molecular dynamics simulations of a membrane protein stabilizing polymer," 2011, vol. 27, issue 17, pp. 10523-10537.*
John C. Shelley et al., "A coarse grain model for phospholipid simulations," Journal of Physical Chemistry B, 2001, vol. 105, pp. 4464-4470.*
Vagelis A. Harmandaris et al., "Predicting polymer dynamics at multiple length and time scales," 2009, Soft Matter, vol. 5, pp. 3920-3926.*

(Continued)

*Primary Examiner* — Kamini S Shah
*Assistant Examiner* — Russ Guill
(74) *Attorney, Agent, or Firm* — Birch, Stewart, Kolasch & Birch, LLP

(57) ABSTRACT

A simulation method for a macromolecular material comprises: a first calculation process for computing a Rouse parameter of a coarse-grained model; a second calculation process for computing a Rouse parameter of the a all-atom model; and a convert process for converting a unit system employed in a molecular dynamics calculation made by the use of the coarse-grained model into a unit system employed in the macromolecular chain, based on the Rouse parameter of the coarse-grained model and the Rouse parameter of the all-atom model.

20 Claims, 18 Drawing Sheets

(56) References Cited

PUBLICATIONS

Christine Peter et al., "Multiscale simulation of soft matter systems from the atomistic to the coarse grained level and back," 2009, Soft Matter, vol. 5, pp. 4357-4366.*

Groot R D et al: "Dissipative particle dynamics: bridging the gap between atomistic and mesoscopic simulation", Journal of Chemical Physics, American Institute of Physics, US, vol. 107, No. 11, Sep. 15, 1997, XP009125803, pp. 4423-4435.

Padding J T et al: "Time and length scales of polymer melts studied by coarse-grained molecular dynamics simulations", Journal of Chemical Physics, American Institute of Physics, US, vol. 117, No. 2, Jul. 8, 2002, XP008133117, pp. 925-943.

Padding J T et al: "Topical Review; Systematic coarse-graining of the dynamics of entangled polymer melts: the road from chemistry to rheology . . . rheology", Journal of Physics: Condensed Matter, Inst of Physics Publishing, Bristol, GB, vol. 23,No. 23, May 25, 2011, XP020205308, pp. 233101.

Vagelis A. Harmandaris: "Atomistic Molecular Dynamics Simulations of Polymer Melt Viscoelasticity", PhD Thesis, Jan. 1, 2001, XP055125253, pp. 1-197.

\* cited by examiner

SIMULATION METHOD FOR MACROMOLECULAR MATERIAL

BACKGROUND OF THE INVENTION

The present invention relates to a computer simulation method for a macromolecular material, more particularly to a method for converting a unit system used in a molecular dynamics calculation performed by the use of a coarse-grained model into a unit system used in a macromolecular chain of the macromolecular material.

In recent years, in order to develop or design rubber compositions, there has been proposed a computer simulation method for simulating behaviors of a macromolecular material in which a coarse-grained model of a macromolecular chain modeled by a plurality of beads is defined and, using such coarse-grained models disposed in a virtual space, a molecular dynamics calculation to simulate behaviors of the macromolecular chains is performed.

In such a molecular dynamics calculation utilizing a coarse-grained model, a unit system (e.g. time, length, mass, etc.) different from that in the real macromolecular chain is employed. Accordingly, in order to know the actual phenomenon or behaviors expected in the real macromolecular chain from the simulation result based on the coarse-grained model, namely, based on the different unit system, it is necessary to convert the unit system from that in the simulation to that in the real macromolecular chain.

Until now, therefore, through an experiment using the actual macromolecular material, a physical quantity (e.g. relaxation time) of the macromolecular chain is measured. Then, using the obtained physical quantity, the conversion of the unit system is made. Such a conversion based on the experimental result is costly and takes time. Further, if the macromolecular material does not exist yet in reality or is not readily available, the conversion is almost impossible.

As another method to avoid a conversion between different unit systems, it is conceivable to use an all-atom model instead of a coarse-grained model in order to represent a macromolecular chain in a computer simulation method.
In such a method, however, the scale of computation becomes very large, and the computational costly and time are increased.

SUMMARY OF THE INVENTION

It is therefore, an object of the present invention to provide a computer simulation method for a macromolecular material, in which a molecular dynamics calculation is performed by the use of a coarse-grained model and a unit system employed in the molecular dynamics calculation can be readily converted into a unit system in the real macromolecular chain without the need for the experimental measurement.

According to the present invention, a computer simulation method for a macromolecular material comprises:

a process in which a coarse-grained model of a macromolecular chain modeled by a plurality of beads is defined, a process in which, using the coarse-grained model disposed in a predetermined virtual space, a molecular dynamics calculation is performed, a first calculation process in which Rouse parameters of the coarse-grained model are computed, a process in which, an all-atom model of an arbitrary macromolecular chain modeled by a plurality of atoms is defined, a process in which, using the all-atom model disposed in a predetermined virtual space, a molecular dynamics calculation is performed by the computer, a second calculation process in which Rouse parameters of the all-atom model are computed, a convert process in which, using the obtained Rouse parameters of the coarse-grained model and the obtained Rouse parameters of the all-atom model, a unit system employed in the molecular dynamics calculation performed by the use of the coarse-grained model is converted into a unit system employed in the macromolecular chain, wherein the second calculation process comprises an entire-length calculation process for obtaining the entire length of the all-atom model, and the entire-length calculation process comprises a process in which the position of a carbon atom of the all-atom model at one end thereof is fixed relatively to the virtual space, a process in which a carbon atom of the all-atom model at the other end thereof is forced to move away from said one end, while performing the molecular dynamics calculation, so that the all-atom model is forcibly stretched, a process in which the forcibly stretched all-atom model is structurally stabilized by performing a calculation according to a molecular mechanics method, and a process in which the distance between said one end and other end of the all-atom model structurally stabilized is computed as the entire length Lf of the all-atom model.

DESCRIPTION OF THE PREFERRED EMBODIMENTS

Embodiments of the present invention will now be described in detail in conjunction with accompanying drawings.

Figure 1:
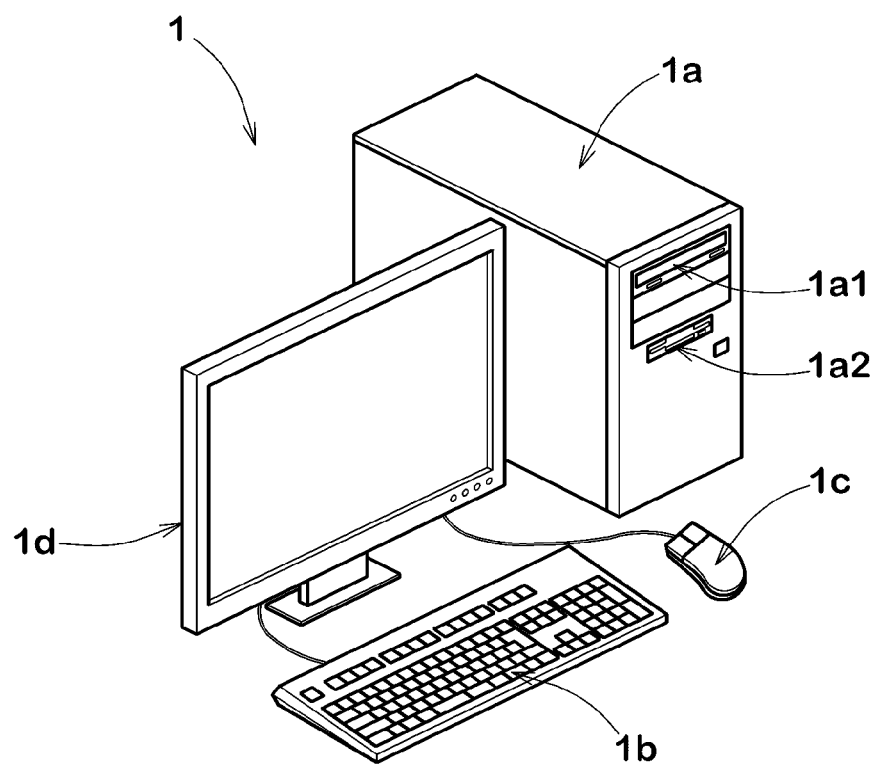
FIG. 1 shows a computer implementing a simulation method for a macromolecular material according to the present invention.

The computer simulation method for a macromolecular material in this embodiment is used to simulate and evaluate behaviors of the macromolecular material by the use of a computer as shown in FIG. 1, Here, the term "macromolecular material" encompasses rubber, resin, elastomer and the like.

As shown in FIG. 1 for example, the computer 1 comprises a main body 1a, a keyboard 1b, a mouse 1c and a display 1d. The main body 1a comprises an arithmetic processing unit (CPU), memory, storage devices such as magnetic disk, disk drives 1a1 and 1a2 and the like. In the storage device, programs/software for carrying out the simulating method are stored.

Figure 2:
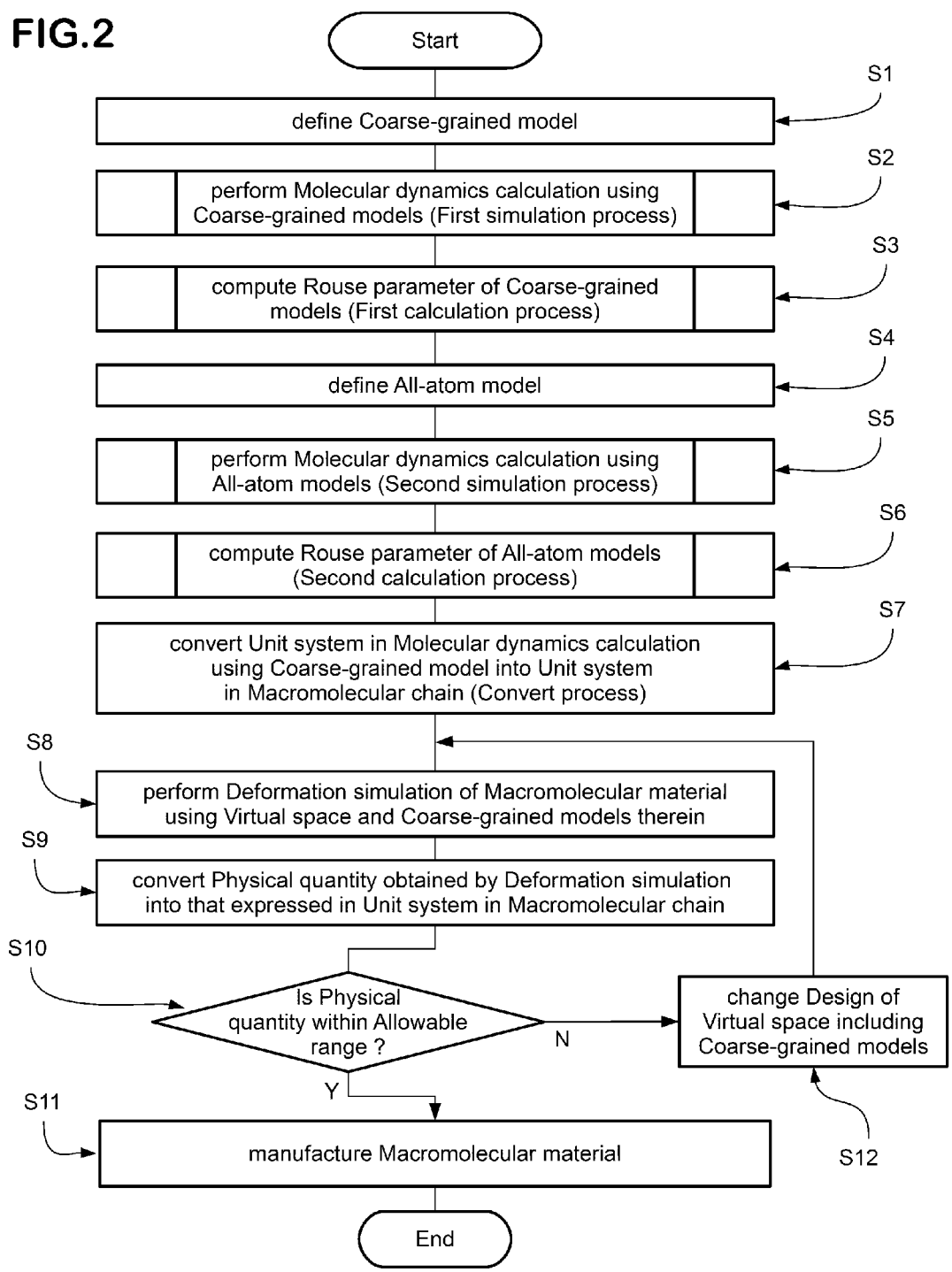
FIG. 2 is a flow chart of the simulation method in this embodiment.

FIG. 2 shows a flowchart of the computer simulation method in this embodiment.

Process S1

Figure 3:
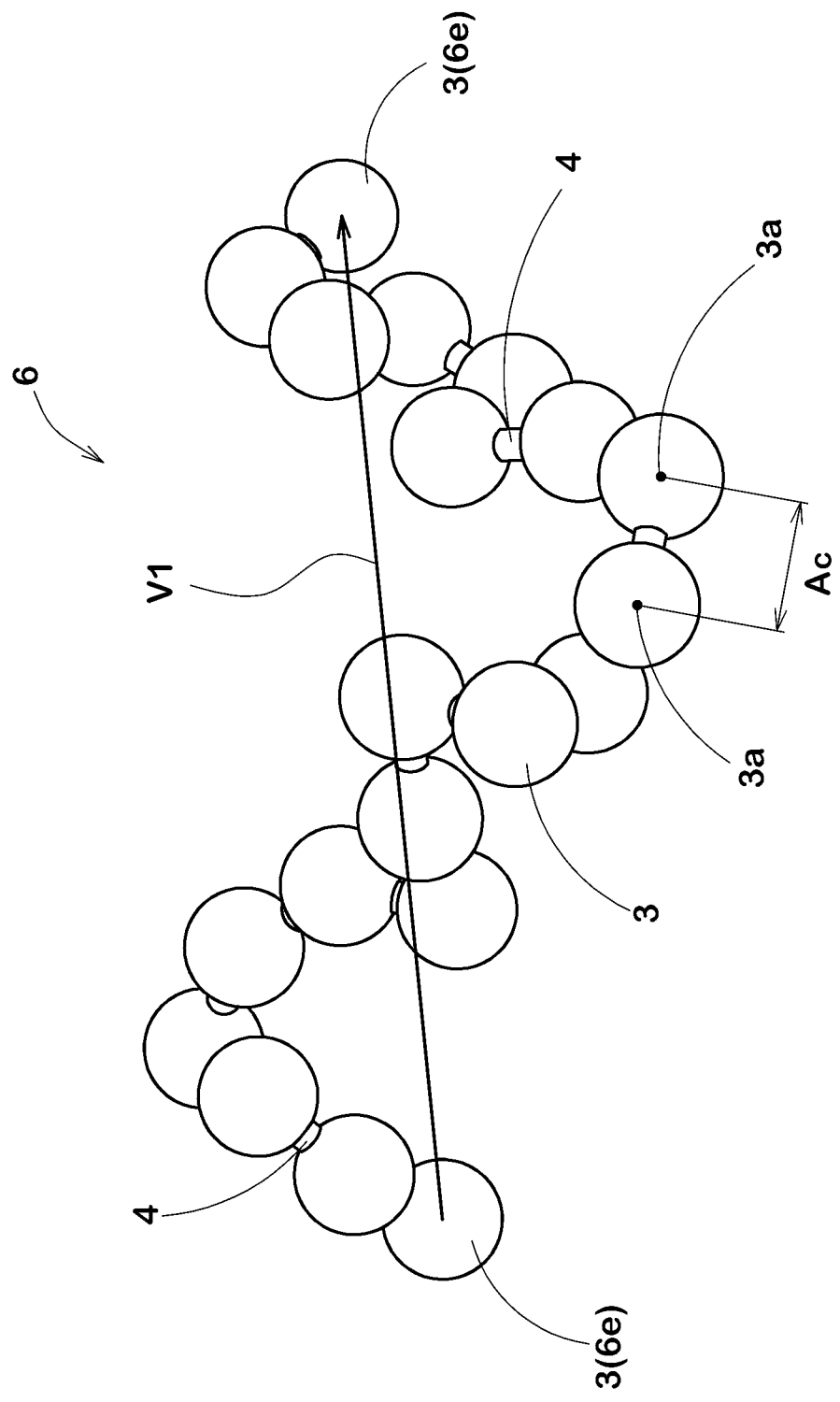
FIG. 3 is a diagram showing a coarse-grained model.

In this process S1, as shown in FIG. 3, a coarse-grained model 6 of a macromolecular chain which is modeled by a plurality of beads 3, is defined in the computer 1.

In this embodiment, the coarse-grained model 6 has a three-dimensional straight-chain structure.

The coarse-grained model 6 corresponds to numerical data used in a molecular dynamics calculation and stored in the computer 1. The coarse-grained model 6 is used in the after-mentioned deformation simulation as coarse-grained models of macromolecular chains of the macromolecular material as the analysis object.

In such a molecular dynamics calculation, the beads 3 are treated as material points in a motion equation. Namely, on each of the beads 3, parameters such as the mass, diameter, electrical charge and initial stage coordinate are defined, and the parameters are stored in the computer 1 as numerical data.

Further, between the adjacent beads 3 of the coarse-grained model 6, there is defined a coupling potential defined by the use of an equilibrium length therebetween. By such coupling potential, a joining chain 4 between the beads 3 is defined. Here, the equilibrium length corresponds to a bond distance between the beads 3.

If this bond distance is changed, owing to the joining chain 4, it can retain the original equilibrium length. Thereby, the coarse-grained model 6 can maintain its three-dimensional straight-chain structure.

Incidentally, the equilibrium length is defined as the distance between the centers 3a and 3a of the beads 3 concerned. The coupling potential or the joining chain 4 can be defined according to the following non-patent document 1.

[Non-Patent Document 1]
Kurt Kremer & Gary S. Grest "Dynamics of entangled linear polymer melts: A molecular-dynamics simulation", J. Chem Phys. vol. 92, No. 8, 15 Apr. 1990

First Simulation Process S2

In this process S2, using the coarse-grained models disposed in a predetermined virtual space 8, the molecular dynamics calculation is performed by the computer 1.

Figure 4:
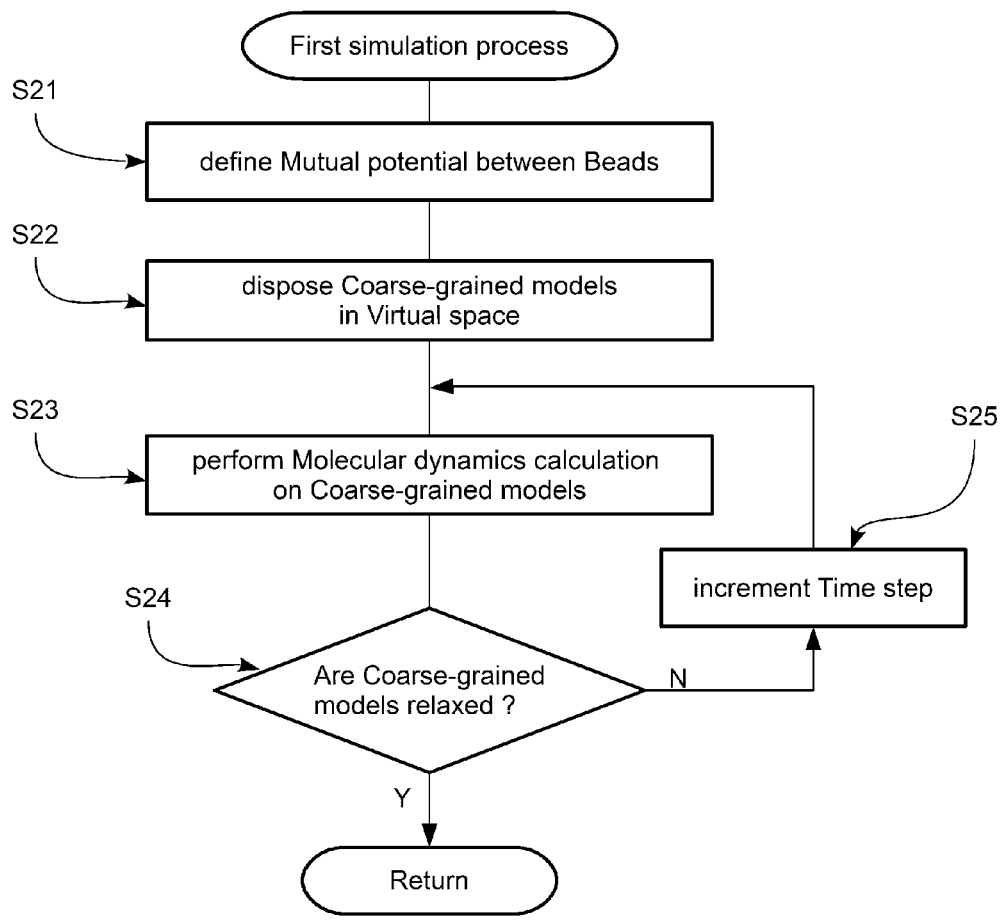
FIG. 4 is a flow chart of the first simulation process in this embodiment.

FIG. 4 shows a flowchart of the first simulation process S2 in this embodiment.

Process S21

Figure 5:
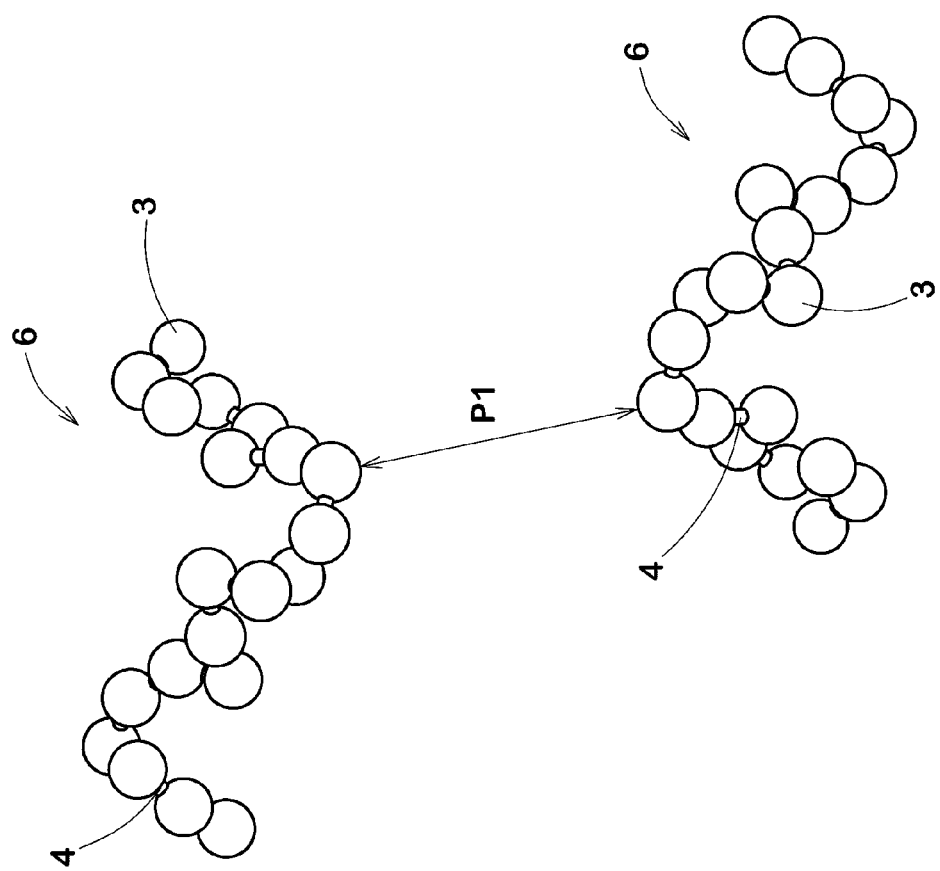
FIG. 5 is a diagram for explaining a potential defined on the coarse-grained model.

In this process S21, as shown in FIG. 5, a mutual potential P1 between two beads 3 which is a function of the distance therebetween is defined.

In this embodiment, used as the mutual potential P1 is the LJ (Lennard-Jones) potential given by the following expression (5).

$$P = \begin{cases} 4\varepsilon\left(\left(\dfrac{\sigma}{r_{ij}}\right)^{12} - \left(\dfrac{\sigma}{r_{ij}}\right)^{6}\right) & r_{ij} < r_c \\ 0 & r_{ij} \geq r_c \end{cases} \quad \text{expression (5)}$$

wherein
$r_{ij}$ is the distance between the beads concerned,
$r_c$ is a cutoff distance,
$\varepsilon$ is a coefficient relating to the intensity of the mutual potential, and
$\sigma$ is a distance relating to the mutual potential (namely, the diameter of Lennard-Jones sphere known in the field of the molecular dynamics).

Incidentally, the distance $r_{ij}$ and the cutoff distance $r_c$ are defined based on the centers 3a of the beads 3.

Such mutual potential P1 exerts an attracting force or repulsive force between the beads 3 when the distance $r_{ij}$ therebetween is less than the cutoff distance $r_c$.

If the distance $r_{ij}$ becomes equal to or more than the cutoff distance $r_c$, the mutual potential P1 is zero and the attracting force or repulsive force between the beads 3 becomes zero.

Such mutual potential P1 can approximate the molecular dynamics calculation to the actual molecular motion of the macromolecular material.

Based on the above-mentioned non-patent document 1, the values of $\varepsilon$, $\sigma$ and rc can be defined as follows.
$\varepsilon$: 1.0
$\sigma$: 1.0
rc: $2^{1/6}$ The mutual potential P1 is computed and stored in the computer 1.

Process S22

In this process S22, the coarse-grained models 6 are disposed in the virtual space 8 having a predetermined volume.

The virtual space 8 correspond to a minute fraction of the macromolecular material as the analysis object.

Figure 6:
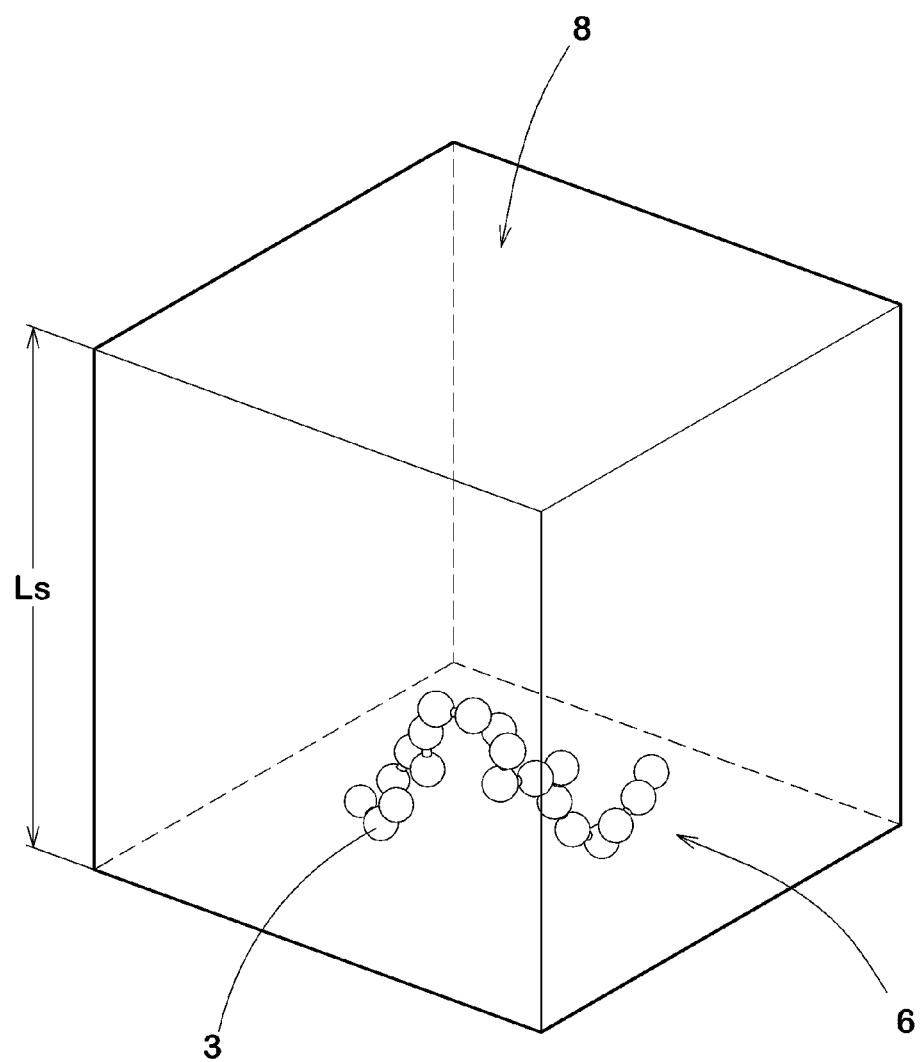
FIG. 6 is a perspective view of a virtual space and the coarse-grained model disposed therein.

In this embodiment, as shown in FIG. 6, the length Ls of each side of the virtual space 8 is defined based on the number density (=0.85) of the beads within the system and the number of the beads 3 disposed in the virtual space 8 according to the non-patent document 1.

For example, the length Ls of each side is 18$\sigma$, and 100 to 400 coarse-grained models 6 are disposed in the virtual space 8. Preferably, the coarse-grained models 6 are arranged according to the Monte Carlo method.

Data about the beads 3 of the coarse-grained models 6 such as coordinates are stored in the computer 1.

Process S23

In this process S23, with respect to the coarse-grained models 6, the molecular dynamics calculation is performed by the computer 1.

In the molecular dynamics calculation in this embodiment, the Newton's motion equation is utilized on the premise that all the coarse-grained models 6 within the virtual space 8 conform to the classical dynamics for a given length of time.

Then, motions of all the beads 3 at each time step are tracked and stored in the computer 1.

As to the conditions of the molecular dynamics calculation, the number, volume and temperature of the beads 3 within the system are respectively kept at constant values during the calculation.

Process S24

In this process S24, the computer 1 judges if the initial arrangement of the coarse-grained models 6 has been fully relaxed.

If fully relaxed, the process goes to the first calculation process S3.

If not yet fully relaxed, the time step is incremented by a unit time. (Process S25)

Then, the process S23 and process S24 are repeated.

Therefore, in the first simulation process S2, an equilibrium state (structurally relaxed state) of the coarse-grained models 6 can be obtained certainly.

First Calculation Process S3

In this process S3, Rouse parameters of the coarse-grained models 6 in the relaxed state are computed and stored in the computer 1.

Here, the Rouse parameters are parameters of Rouse model known in the field of polymer physics.

In this embodiment, the length parameter $b_c$ (unit: $\sigma$), time parameter $\tau_c$ (unit: $\tau$), and friction parameter $\zeta_c$ (unit: $\mu/\tau$) are computed using the numerical data stored at every unit time in the molecular dynamics calculation on the coarse-grained models 6 performed in the process S23.

Figure 7:
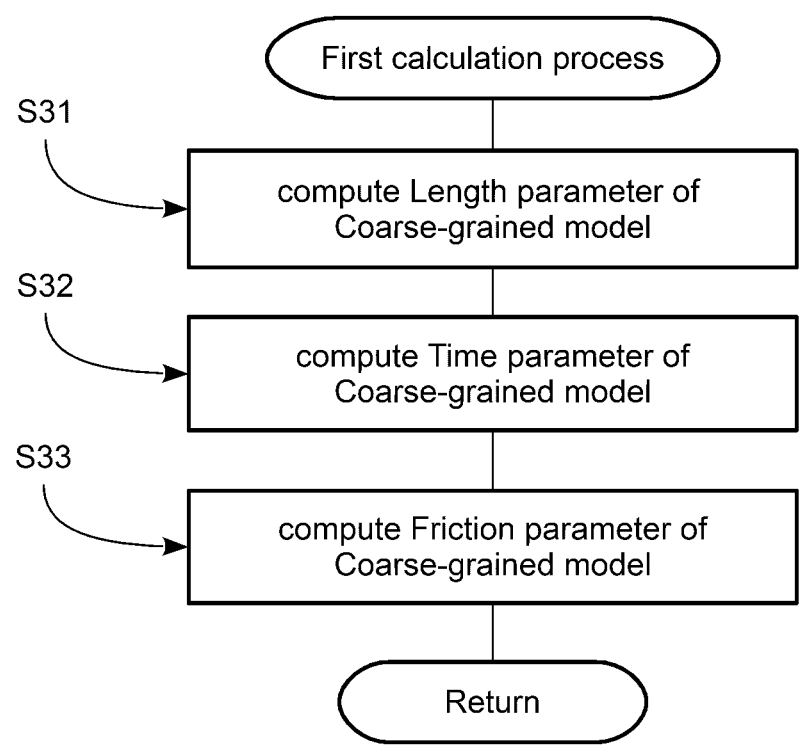
FIG. 7 is a flow chart of the first calculation process in this embodiment.

FIG. 7 shows a flowchart of the first calculation process S3 in this embodiment.

Process S31

In this process S31, the length parameter bc (unit:$\sigma$) of the coarse-grained models 6 is computed by the computer 1.

The length parameter bc is given by the following expression (1).

$$b_c = \frac{\langle R_c^2 \rangle}{L_c} \quad \text{expression (1)}$$

$$L_c = A_c \times (N_c - 1)$$

wherein $\langle R_c^2 \rangle$ is the ensemble average relating to a length $R_c$,
$L_c$ is the entire length of the coarse-grained model,
$A_c$ is an equilibrium length between the beads, and
$N_c$ is the number of the Rouse beads per one coarse-grained model.

The length $R_c$ is of the end-to-end vector V1 from one end 6e to the other end 6e of the coarse-grained model 6 as shown in FIG. 3. Incidentally, the length $R_c$ is between the centers 3a of the beads 3.

The ensemble average $\langle R_c^2 \rangle$ is obtained as follows. First, for each of the coarse-grained models 6, the square of the length $R_c$ of the end-to-end vector at each time step is averaged over the entire time period during which the molecular dynamics calculation is performed. Then, such time average is averaged over all of the coarse-grained models 6 to obtain the ensemble average as the $\langle R_c^2 \rangle$.

The entire length $L_c$ is the total length of the joining chains 4 included in one coarse-grained model 6.

Here, it is assumed that all the coarse-grained models 6 have the same entire-length. However, if the coarse-grained models 6 have different entire-lengths, their average may be used.

The entire length $L_c$ may be obtained as the product of the equilibrium length $A_c$ between beads 3 and the number ($N_c-1$) of the joining chains 4.

Here, a local minimum of the coupling potentials defined on the joining chains 4 is assigned with the equilibrium length $A_c$.

The obtained length parameter $b_c$ is stored in the computer 1.

Process S32

In this process S32, the time parameter $\tau_c$ (unit:$\tau$) of the coarse-grained model 6 is computed and stored in the computer 1.

Figure 8:
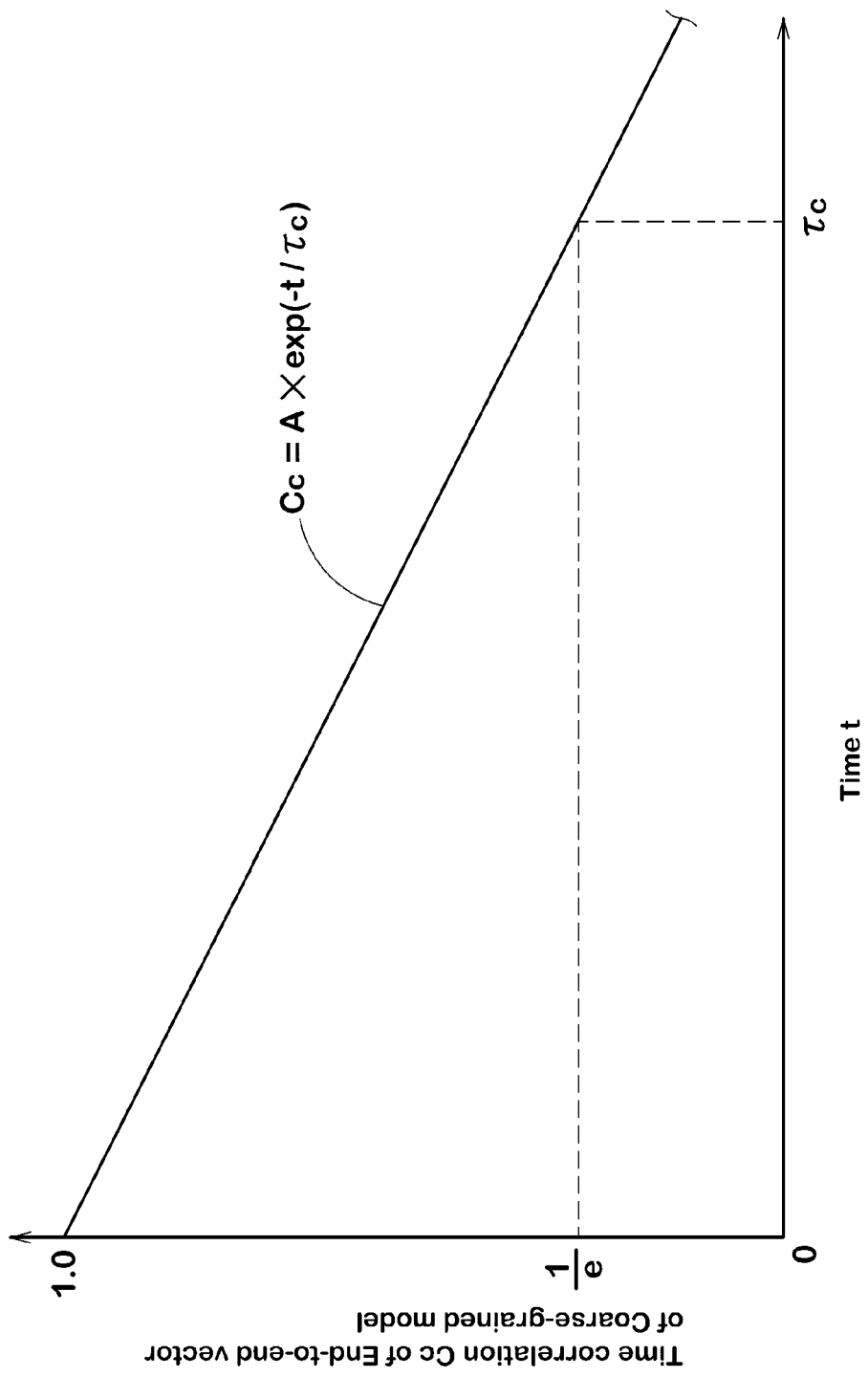
FIG. 8 is a graph of a time correlation function of the end-to-end vector of the coarse-grained model.

FIG. 8 is a graph of a function Cc of the auto-correlation or time correlation of the length $R_c$ of the end-to-end vector V1 of the coarse-grained model 6 and the time t.

The time parameter $\tau_c$ is defined by the time at which the end-to-end vector V1 becomes to have no time correlation, namely, the time required for the value of the function Cc to decrease to 1/e. This is based on decay in the atomic theory. Thus the time parameter $\tau c$ is a constant.

Such time parameter $\tau_c$ can be obtained from the time correlation function Cc approximated by the right-hand side of the following expression (6).

$$C_c = A \times \exp(-t/\tau_c) \quad \text{expression (6)}$$

wherein

A is a fitting parameter, and
t is the time.

Process S33

In this process S33, the friction parameter $\zeta_c$ (unit: $\mu/\tau$) of the coarse-grained model 6 is computed and stored in the computer 1.

The friction parameter $\zeta_c$ is defined by the following expression (2).

$$\xi_c = \frac{3\pi^2 \times k_B \times T \times \tau_c}{N_c^2 \times b_c^2} \quad \text{expression (2)}$$

wherein $b_c$ is the length parameter of the coarse-grained model,
$\tau_c$ is the time parameter of the coarse-grained model,
$N_c$ is the number of the Rouse beads per one coarse-grained model,
$k_B$ is the Boltzmann's constant, and
T is the absolute temperature.

As explained above, the length parameter $b_c$ and the time parameter $\tau_c$ are mathematical values obtained through the process S31 and process S32.

The number $N_c$ is the counted number of the beads 3 of the concerned coarse-grained model 6. But, the number $N_c$ of the beads may be obtained as a quotient of the entire length $L_c$ obtained from the expression (1) divided by the length parameter $b_c$.

In the first calculation process S3, therefore, the Rouse parameters (length parameter $b_c$, time parameter $\tau_c$ and friction parameter $\zeta_c$) of the coarse-grained model 6 are obtained.

Process S4

Next, an all-atom model of an arbitrary macromolecular chain of the macromolecular material as the analysis object is defined in the computer 1.

Figure 9:
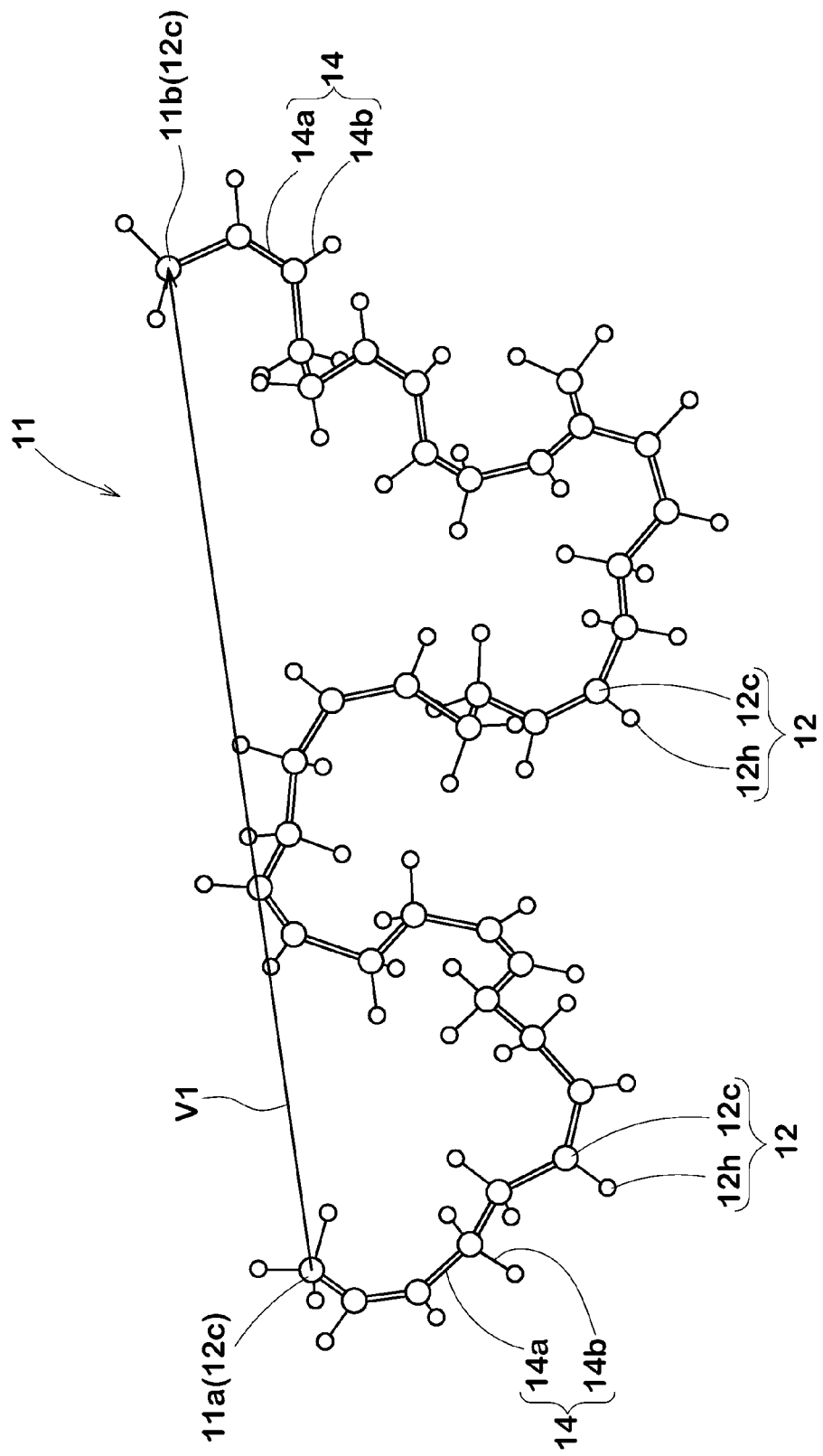
FIG. 9 is a diagram of the all-atom model.

In FIG. 9, an example of the macromolecular chain in this embodiment (cis-1,4 polybutadiene whose degree of polymerization is 2070 for example. Hereinafter, the polybutadiene) is shown.

In the all-atom model 11, all the atoms which may include carbon atoms 12c and hydrogen atom 12h, are respectively modeled by particle models 12.

In a simulation based on a molecular dynamics calculation, the particle models 12 are treated as material points in a motion equation. Namely, on each particle model 12, parameters such as the mass, diameter, electrical charge and initial stage coordinate are defined, and the parameters are stored in the computer 1 as numerical data.

Further, between the particle models 12, joining chains 14 are defined. The joining chain 14 is treated as a spring having an equilibrium length and a spring constant.
Such data are also stored in the computer 1.

In this embodiment, the joining chains 14 include a main joining chain 14a between two carbon atoms 12c, and a side joining chain 14b between a carbon atom 12c and a hydrogen atom 12h.
On the all-atom model 11, there are defined a bond length between two particle models 12, a bond angle formed by three particle models 12 which are successive through the joining chains 14, and a dihedral angle formed by three successive particle models 12 of four successive particle models 12 which are successive through the joining chains 14. Thus, the all-atom model 11 is defined as having such three-dimensional structure.

When an external force or internal force is applied to the all-atom model 11, the bond length, bond angle and dihedral angle may be changed, and thereby the three dimensional structure of the all-atom model 11 may be changed too.
such modeling can be made by utilizing an application software J-OCTA created by JSOL corporation for example.

Second Simulation Process S5

In this process S5, using the all-atom models arranged in a predetermined virtual space 16, a molecular dynamics calculation is performed by the computer 1.

Figure 10:
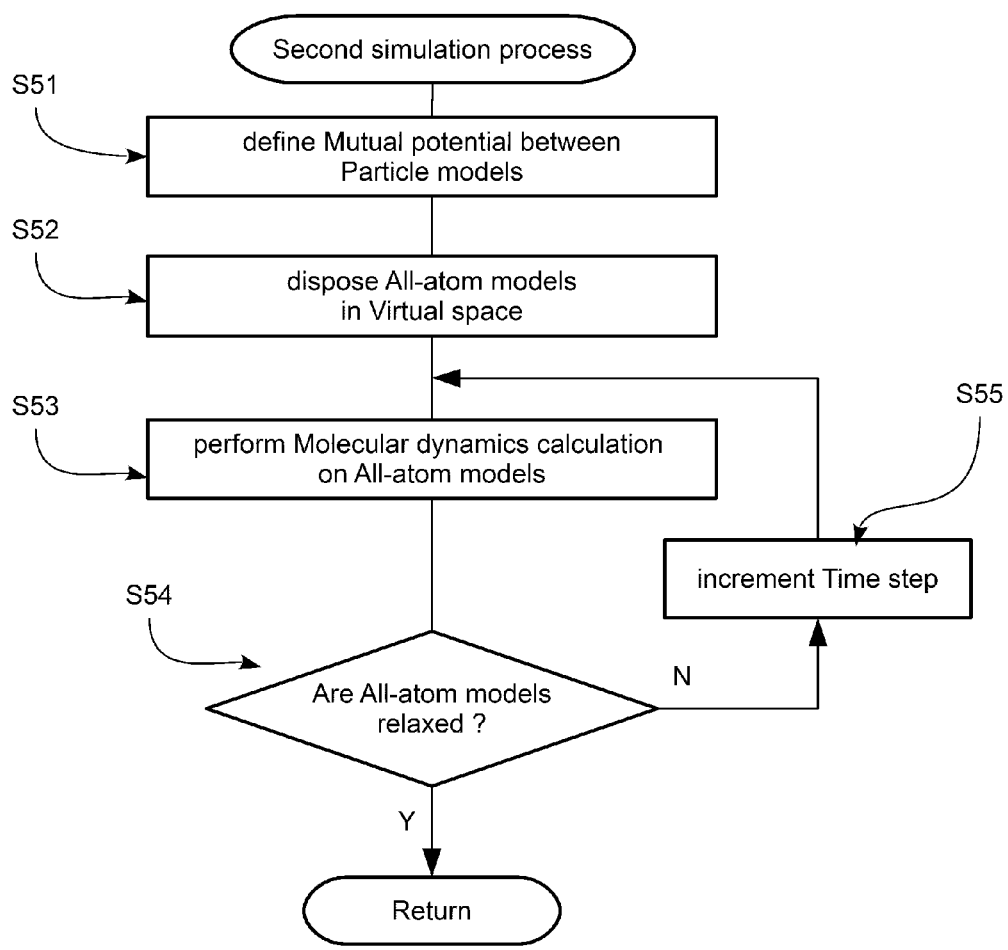
FIG. 10 is a flow chart of the second simulation process in this embodiment.

FIG. 10 shows a flowchart of the second simulation process S5 in this embodiment.

Process S51

In this process S51, a mutual potential P2 between two particle models 12 is defined.

As the mutual potential P2, the above-mentioned LJ (Lennard-Jones) potential given by the expression (5) is used.

Figure 11:
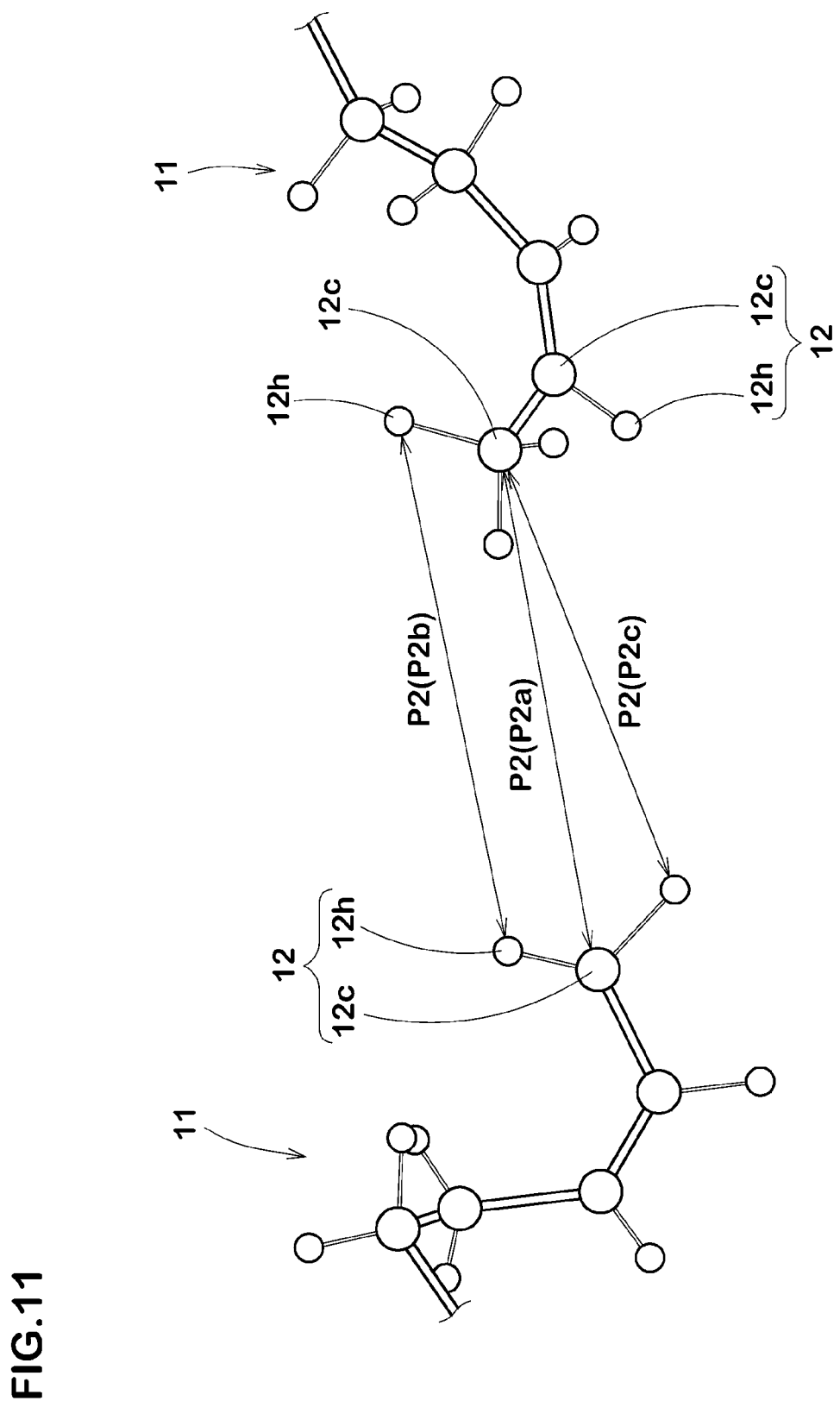
FIG. 11 is a diagram for explaining a potential defined on the all-atom model.

The mutual potential P2 includes, as shown in FIG. 11, a first mutual potential P2a between two carbon atoms 12c, a second mutual potential P2b between two hydrogen atoms 12h, and a third mutual potential P2c between a carbon atom 12c and a hydrogen atom 12h.

In each of the potentials P2a, P2b and P2c, the above-mentioned distance σ and the cutoff distance $r_c$ in the expression (5) may be determined arbitrarily.
Such mutual potentials P2 are stored in the computer 1.

Process S52

In this process S52, the all-atom models 11 are disposed in the virtual space 16 having a predetermined volume.

Figure 12:
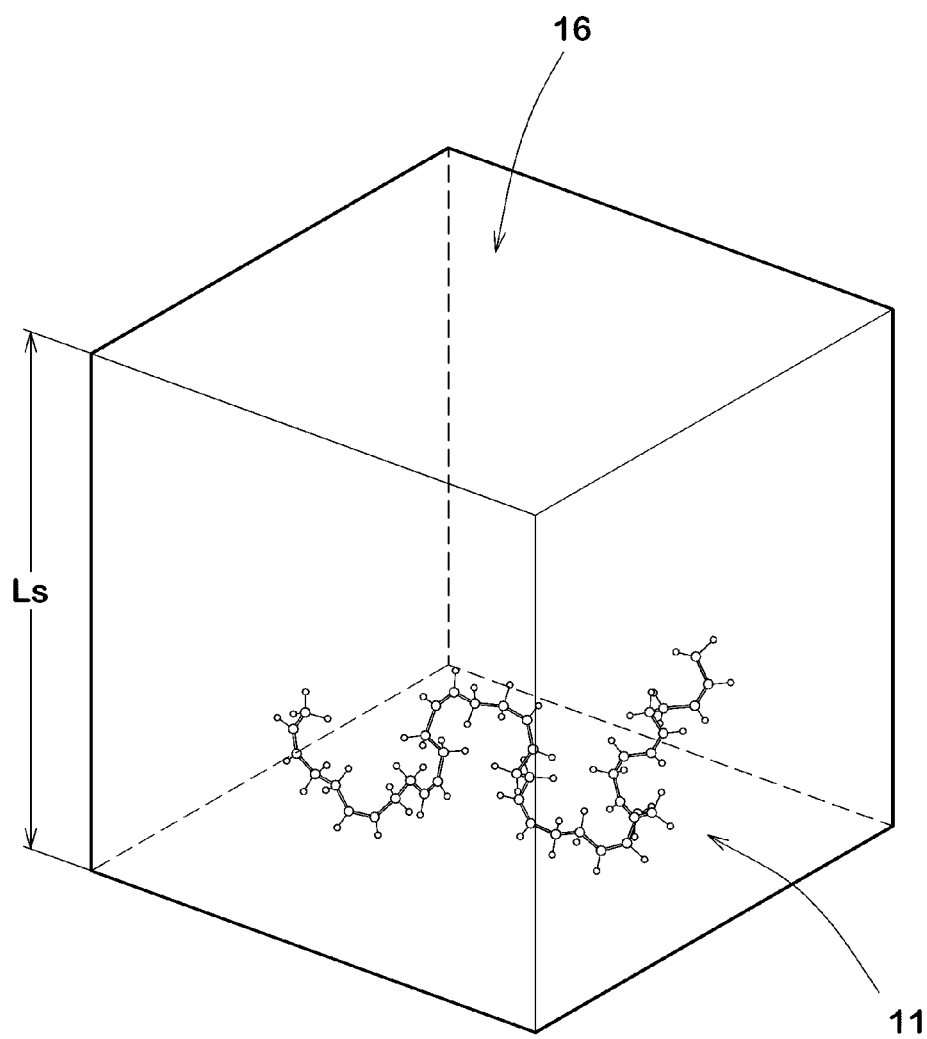
FIG. 12 is a perspective view of a virtual space and the all-atom model disposed therein.

As shown in FIG. 12, the virtual space 16 correspond to a minute fraction of the macromolecular material as the analysis object and is defined in the same manner as in the virtual space 8 shown in FIG. 6.
For example, 10 to 100 all-atom models 11 are disposed in the virtual space 16.
Preferably, such all-atom models 11 are arranged according to the Monte Carlo method.
Data about the particle models 12 of the all-atom models 11 such as coordinates are stored in the computer 1.

Process S53

In this process S53, with respect to the all-atom models 11, the molecular dynamics calculation is performed by the computer 1.

In the molecular dynamics calculation in this embodiment, similarly to the molecular dynamics calculation of the coarse-grained models 6, the Newton's motion equation is utilized on the premise that all the particle models 12 of the all-atom models 11 in the virtual space 16 conform to the classical dynamics for a given length of time.
Then, motions of all particle models 12 at each time step are tracked and stored in the computer 1.
As to the conditions of the molecular dynamics calculation, the number, volume and temperature of the particles within the system are respectively kept at constant values during the calculation.

Process S54

In this process S54, the computer 1 judges if the initial arrangement of the particle models 12 of the all-atom models 11 has been fully relaxed.

If fully relaxed, the process goes to the second calculation process S6.

If not yet fully relaxed, the time step is incremented by a unit time. (process S55)
Then, the process S53 (molecular dynamics calculation) and the process S54 are repeated.

In the second simulation process S5, therefore, an equilibrium state (structurally relaxed state) of the all-atom models 11 can be obtained certainly.

Second Calculation Process S6

In this process S6, the Rouse parameters of the all-atom models in the relaxed state are computed by the computer 1.

In this embodiment, the length parameter $b_f$ (unit: meter), time parameter $\tau_f$ (unit: second) and friction parameter $\zeta_f$ (unit: kilogram/second) of the Rouse parameters are computed using the numerical data stored at every unit time in the molecular dynamics calculation of the all-atom models 11 performed in the second simulation process S5.

Figure 13:
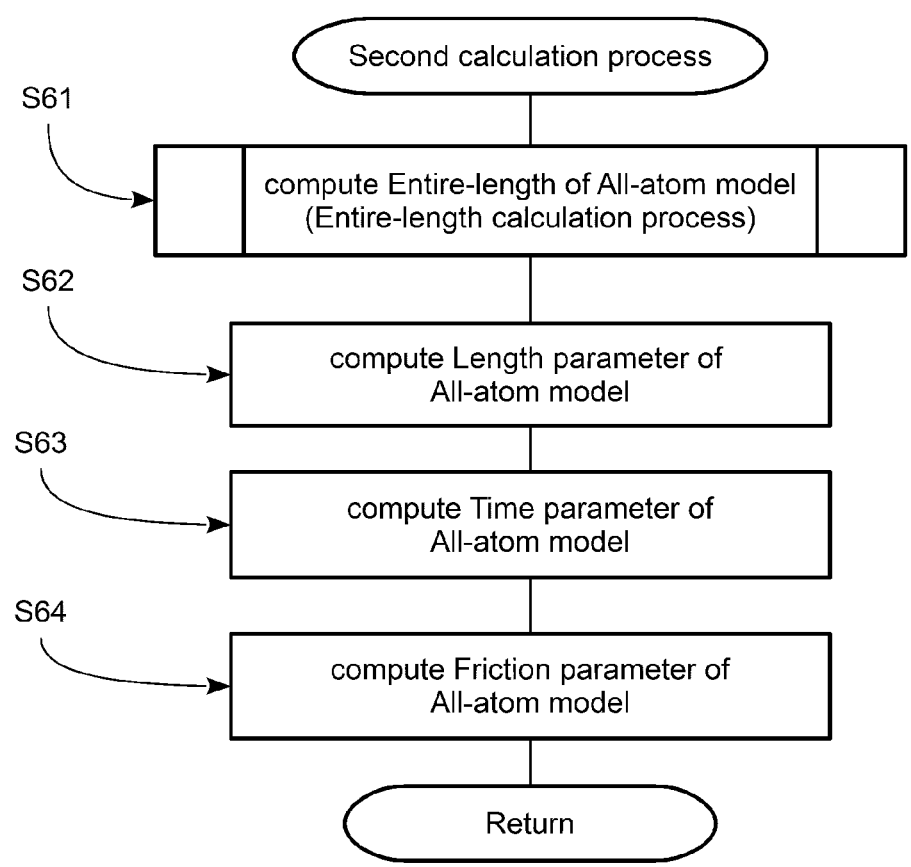
FIG. 13 is a flow chart of the second calculation process in this embodiment.

FIG. 13 shows a flowchart of the second calculation process S6 in this embodiment.

Entire-Length Calculation Process S61

In this process S61, the entire length $L_f$ of the all-atom model 11 is computed by the computer 1.

Figure 14:
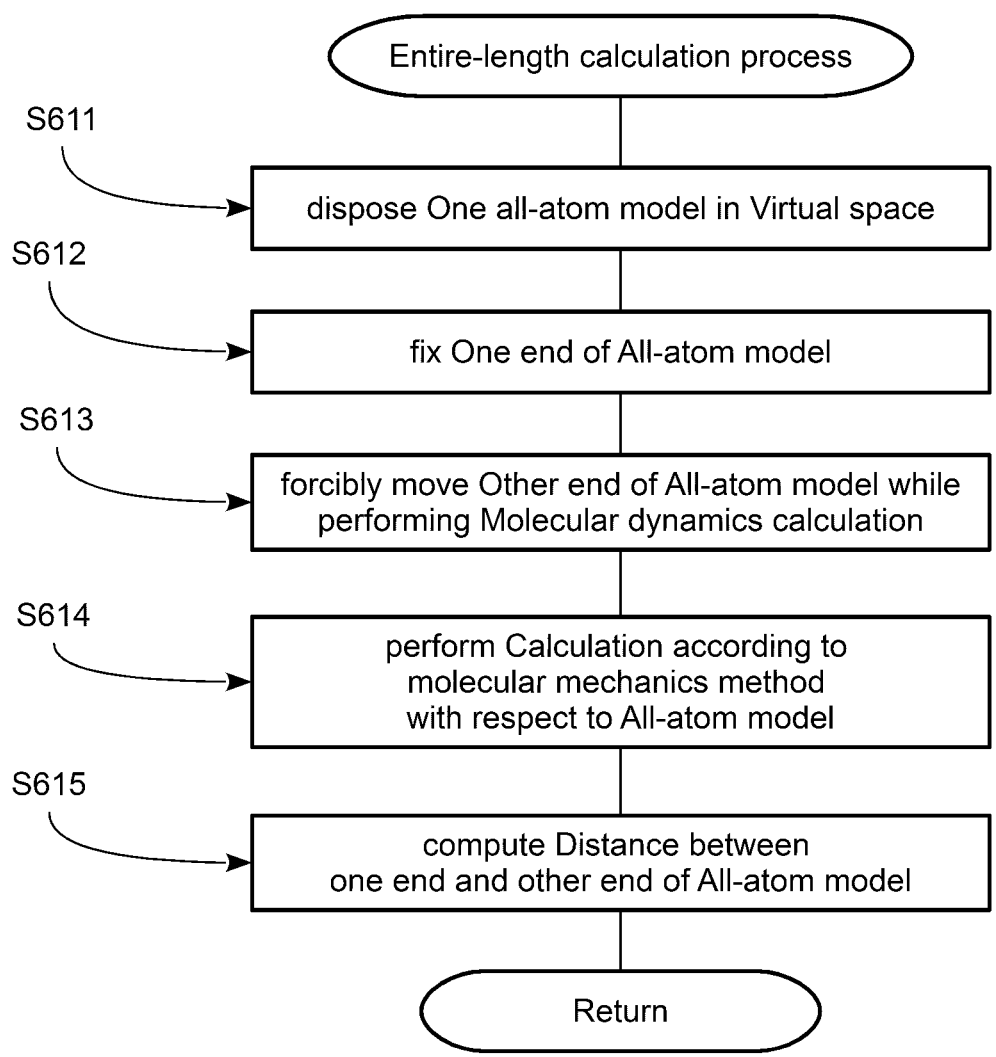
FIG. 14 is a flow chart of the entire-length calculation process in this embodiment.

FIG. 14 shows a flowchart of the entire-length calculation process S61.

Process S611

Figure 15:
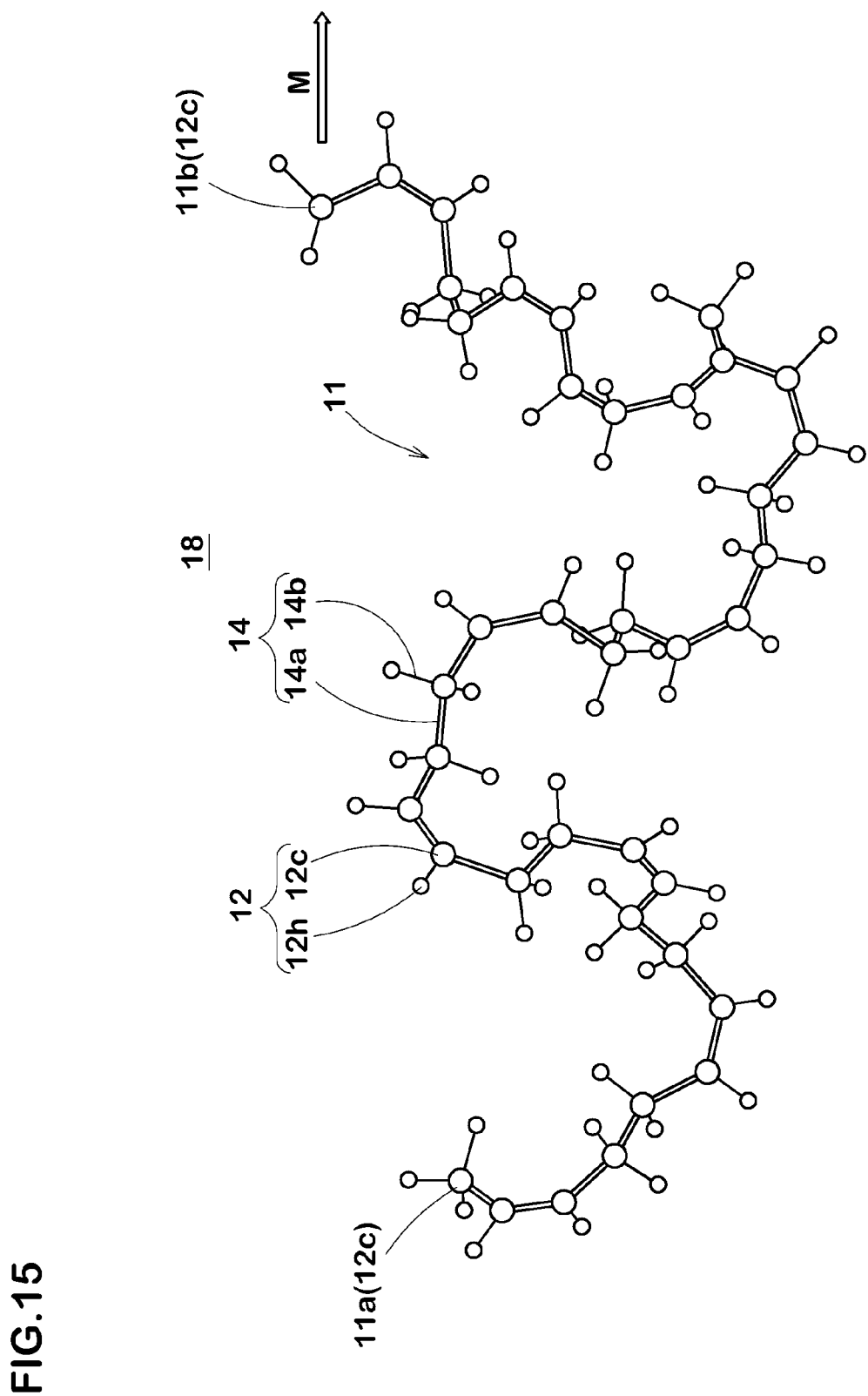
FIG. 15 is a diagram for explaining the all-atom model whose one end is fixed.

In this process S611, as shown in FIG. 15, one all-atom model 11 is disposed in a virtual space 18 having a predetermined volume.

As to the virtual space 18, that having the same structure as the virtual space 16 shown in FIG. 12 is used.
The coordinates of the particle models 12 of the all-atom model 11 are stored in the computer 1.

Process S612

In this process S612, the computer 1 fixes a carbon atom 12c of the all-atom model 11 at its one end relatively to the virtual space 18. More specifically, the computer 1 fixes the coordinate of one of the two carbon atoms 12c of the all-atom model 11 which form the ends 11a and 11b of the all-atom model 11, for example, the coordinate of the carbon atom 12c at one end 11a.
The coordinate value of such fixed end 11a of the carbon atom 12c is stored in the computer 1.

Process S613

In this process 613, the computer 1 forces the other end 11b of the all-atom model 11 to move away from the fixed one end 11a, while performing the molecular dynamics calculation.

In this embodiment, first, on the carbon atom 12c at the other end 11b, a constant velocity motion M to move away from the carbon atom 12c at the fixed one end 11a is defined. The velocity of the constant velocity motion M is for example set in a range of from 500 to 3500 m/s.

Then, based on the potential defined on the all-atom model 11 as the joining chain 14, the computer starts the molecular dynamics calculation. And the motion calculation of the other end 11b of the all-atom model 11 is performed based on the constant velocity motion M defined at the other end 11b.

Figure 16:
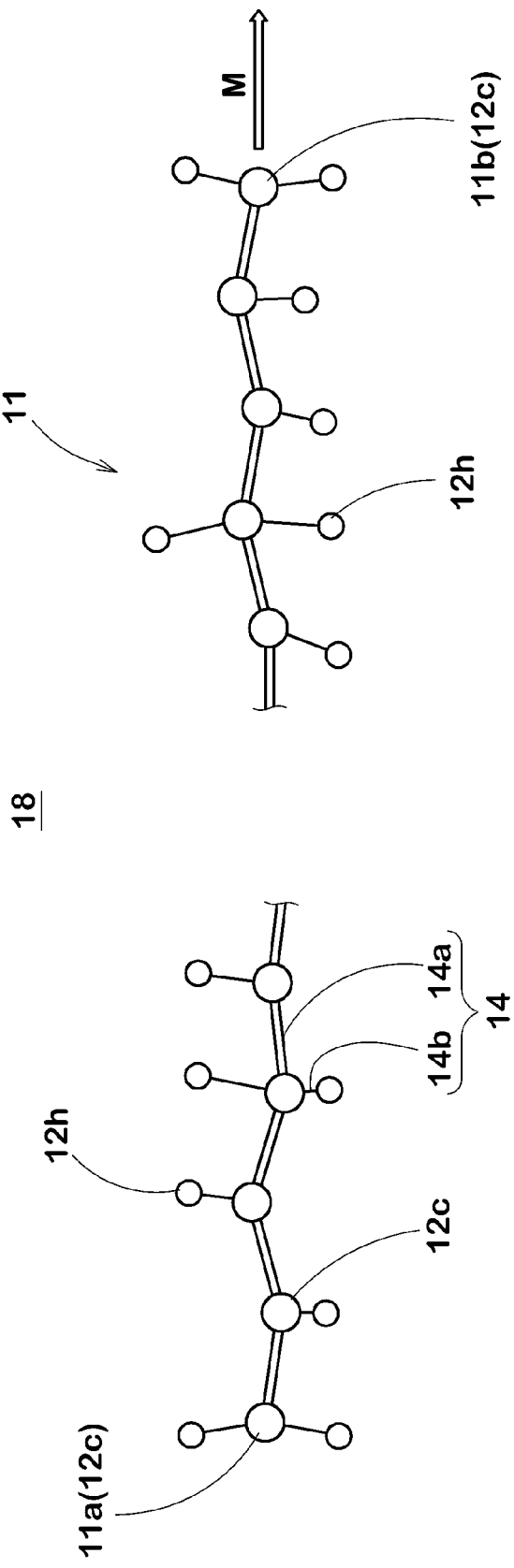
FIG. 16 is a diagram for explaining the all-atom model whose other end is forced to move away from the one end.

As a result, as shown in FIG. 16, the all-atom model 11 is forcibly stretched, and the carbon atoms 12c in the main chain are linearly arranged.

Such stretched state is obtained and defined or stored in the computer.

As explained above, in the process S613 in this embodiment, the motion calculation of the carbon atom 12c is performed by the computer while performing the molecular dynamics calculation, therefore, the motions of the carbon atoms 12c can be calculated in a quick and efficient manner.

The number of steps to perform the molecular dynamics calculation can be arbitrarily determined. But, it is desirable that, when the unit time is one femtosecond for example, the number of steps is in a range of 2500 to 7500.

Process S614

In this process S614, with respect to the forcibly stretched all-atom model 11, the computer 1 performs a calculation according to the molecular mechanics method. Here, the molecular mechanics method is a method for optimizing a molecular structure based on potential energy interacting between atoms. Such calculations based on the molecular mechanics method can be made by utilizing "COGNAC", a program included in an application software J-OCTA created by JSOL Corporation for example.

The calculation according to the molecular mechanics method is preferably continued for example until the potentials defined on the main joining chains 14a are converged within a range of from $6 \times 10^{-11}$ to $8 \times 10^{-11}$ (N).

Figure 17:
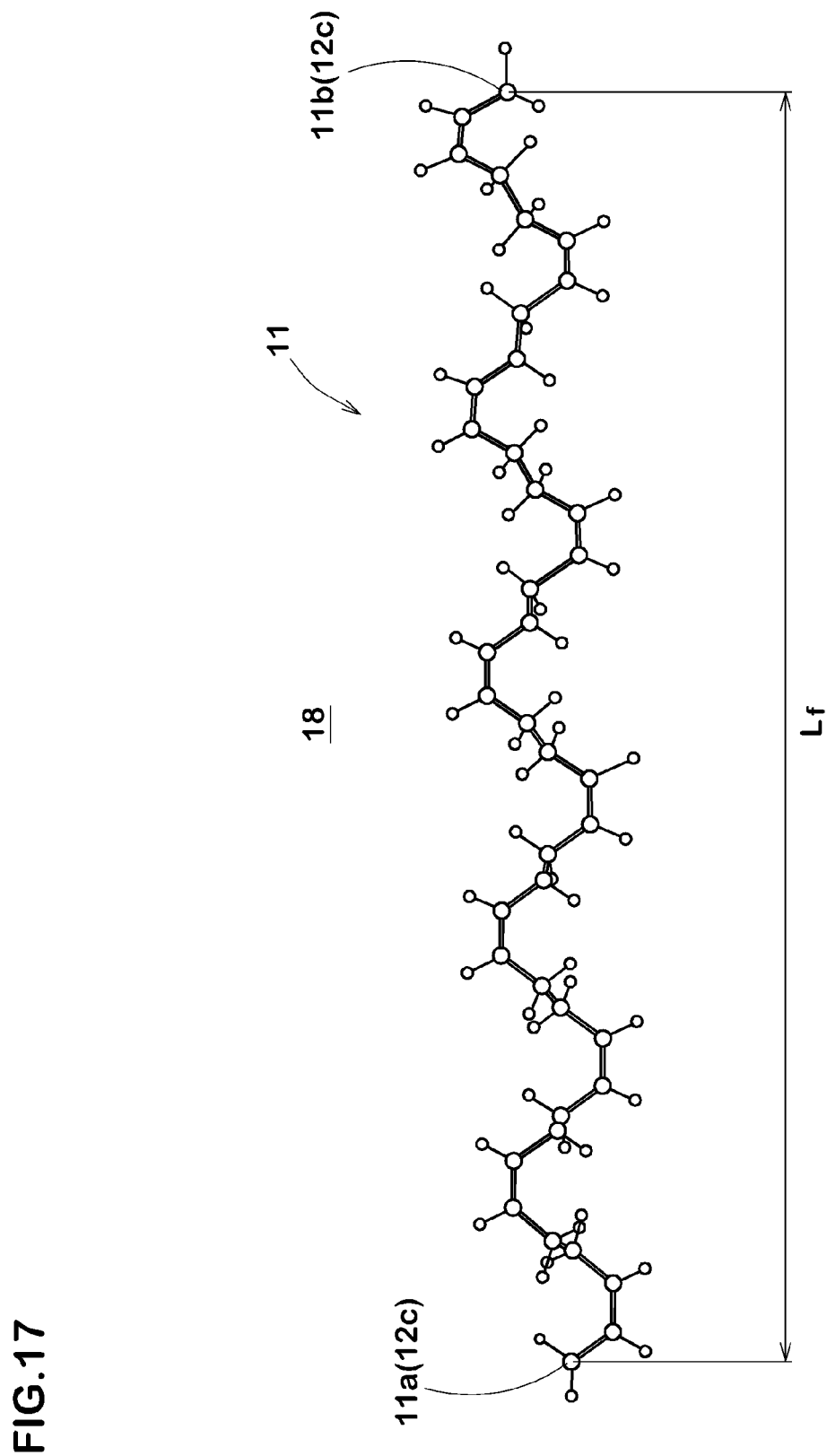
FIG. 17 is a diagram showing the all-atom model after the calculation according to the molecular mechanics method has been made.

In the process S614, therefore, the all-atom model 11 having been stretched in the main chain direction and stabilized in the bond length, bond angle and dihedral angle can be obtained as shown in FIG. 17.

Process S615

In the process S615, the distance between the one end 11a and the other end 11b of the stabilized all-atom model 11, namely, the entire length $L_f$ of the all-atom model 11 is computed and stored in the computer 1.

In the entire-length calculation process S61, therefore, the all-atom model 11 has a stable structure stretched in the main chain direction, and thereby the bond length, bond angle and dihedral angle can be obtained stably without fail. Thus, the entire length $L_f$ of the all-atom model 11 can be computed effectively and certainly.

If the all-atom model 11 is not stretched, it is difficult to compute the entire length $L_f$ of the all-atom model through a molecular dynamics calculation because the all-atom model bends intricately.

Process S62

In this process S62, using the obtained entire length $L_f$, the length parameter $b_f$ of the all-atom model 11 given by the following expression (3) is computed by the computer 1.

$$b_f = \frac{\langle R_f^2 \rangle}{L_f} \qquad \text{expression (3)}$$

wherein $\langle R_f^2 \rangle$ is the ensemble average relating to the length $R_f$.

The length $R_f$ is of the end-to-end vector V2 between the ends 11a and 11b of the all-atom model 11, more concretely between the centers of the carbon atoms 12c at the ends 11a and 11b as shown in FIG. 9.

The ensemble average $\langle R_f^2 \rangle$ is obtained as follows. First, for each of the all-atom models 11, the square of the length $R_f$ at each time step is averaged over the entire time period during which the molecular dynamics calculation is performed. Then, such time average is averaged over all of the all-atom models 11 to obtain the ensemble average as the $\langle R_f^2 \rangle$.

The obtained length parameter $b_f$ is stored in the computer 1.

Process S63

In this process S63, the time parameter $\tau_f$ of the all-atom model 11 is computed by the computer 1.

Figure 18:
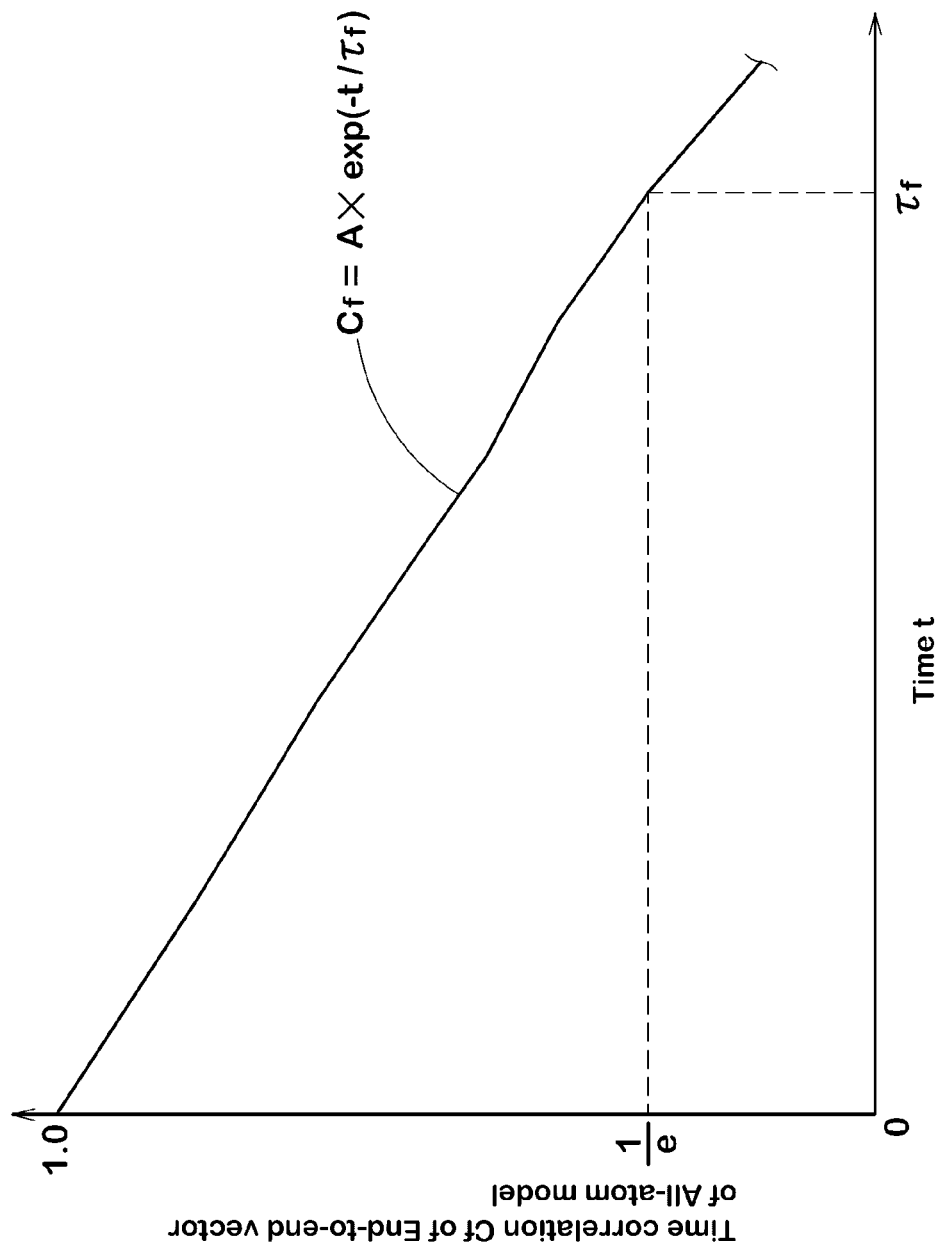
FIG. 18 is a graph of a time correlation function of the end-to-end vector of the all-atom model.

FIG. 18 is a graph of a function $C_f$ of the auto-correlation or time correlation of the length $R_f$ of the end-to-end vector V2 of the all-atom model 11 and the time t.

Similarly to the time parameter $\tau_c$ of the coarse-grained model 6, the time parameter $\tau_f$ is defined by the time required for the value of the function $C_f$ to decrease to 1/e.

Such time parameter $\tau_f$ can be obtained from the time correlation function $C_f$ approximated by the right-hand side of the following expression (7).

$$C_f = A \times \exp(-t/\tau_f) \qquad \text{expression (7)}$$

wherein

A is a fitting parameter, and t is the time

Then, the time parameter $\tau_f$ of the all-atom model 11 is stored in the computer 1.

Process S64

In this process S64, the friction parameter $\zeta_f$ of the all-atom model 11 given by the following expression (4) is computed by the computer 1.

$$\xi_f = \frac{3\pi^2 \times k_B \times T \times \tau_f}{N_f^2 \times b_f^2} \qquad \text{expression (4)}$$

$$N_f = \frac{L_f}{b_f}$$

wherein $b_f$ is the length parameter of the all-atom model, $\tau_f$ is the time parameter of the all-atom model, $N_f$ is the number of the Rouse beads(particle models), $L_f$ is the entire length of the all-atom model, $k_B$ is the Boltzmann's constant, and T is the absolute temperature.

The length parameter $b_f$ and the time parameter $\tau_f$ are mathematical values obtained as explained above.

As to the number $N_f$, the number of the carbon atoms 12c of the all-atom model 11 is assigned therewith. But, for example, the quotient of the entire length $L_f$ obtained through the entire-length calculation process S61 divided by the length parameter $b_f$ may be used instead.

The obtained friction parameter $\zeta_f$ is stored in the computer 1.

In the second calculation process S6, therefore, the Rouse parameters (length parameter $b_f$, time parameter $\tau_f$ and friction parameter $\zeta_f$) of the all-atom model 11 can be obtained certainly.

Convert Process S7

In this process S7, the unit system employed in the molecular dynamics calculation performed by using the coarse-grained model 6 is converted into the unit system employed in the macromolecular chain by the computer 1.

In this embodiment, the units σ (length), τ (time) and μ (mass) are included in the unit system employed in the molecular dynamics calculation performed by using the coarse-grained model 6. In the unit system employed in the macromolecular chain, units meter (length), second (time) and kilogram (mass) are included.

In this embodiment, therefore, a unit length (1σ), unit time (1τ) and unit mass (1μ) are respectively converted into a length (meter), time (second) and mass (kilogram).

In the convert process S7, the conversion is made on the premise that the Rouse parameters of the coarse-grained model 6 are the same as the Rouse parameters of the all-atom model 11 (namely, the macromolecular chain).

For example, if the length parameter $b_c$ of the coarse-grained model 6 is 1σ, and the length parameter $b_f$ of the all-atom model 11 is $1 \times 10^{-9}$ meters, then according to the premise, a unit length 1σ in the molecular dynamics calculation is converted into a length of $1 \times 10^{-9}$ meters in the macromolecular chain.

If the time parameter $\tau_c$ of the coarse-grained model 6 is 5τ, and the time parameter $\tau_f$ of the all-atom model 11 is $5 \times 10^{-11}$ seconds, then a unit time 1τ in the molecular dynamics calculation is converted into a time of $1 \times 10^{-11}$ seconds in the macromolecular chain.

If the friction parameter $\zeta_c$ of the coarse-grained model 6 is 50μ/τ, and the friction parameter $\zeta_f$ of the all-atom model 11 is $1 \times 10^{-11}$ kg/s, then a unit mass 1μ in the molecular dynamics calculation is be converted into a mass of $2.0 \times 10^{-24}$ kilograms in the macromolecular chain.

As explained above, in the simulation method in this embodiment, the unit system in the molecular dynamics calculation using the coarse-grained model 6 is converted into the unit system in the macromolecular chain without the need for an experimental measurement of the physical quantity of the macromolecular chain. Therefore, the cost and time required for the experimental measurement can be eliminated from the simulation method.

In the entire-length calculation process S61, it is possible to efficiently and certainly compute the entire length $L_f$ of the all-atom model 11, therefore, the conversion into the unit system in the macromolecular chain can be further facilitated.

In this embodiment, the all-atom model 11 of polybutadiene is used and the Rouse parameters are obtained. But, needless to say, the all-atom model 11 of another macromolecular chain can be used to obtain the Rouse parameters. In such all-atom model 11 too, in the convert process s7, it is premised that the Rouse parameters of the coarse-grained model 6 are the same as the Rouse parameters of the all-atom model 11. Thereby, in the simulation method according to the present invention, without newly performing a molecular dynamics calculation utilizing the coarse-grained model 6, it is possible to convert the unit system of the coarse-grained model 6 (shown in FIG. 3) into the unit system in the another macromolecular chain without limited to only the unit system of the polybutadiene.

Further, it is possible to use the all-atom model 11 of an arbitrary macromolecular material which does not exist in reality. Therefore, in the second calculation process s6, it is possible to obtain the Rouse parameters of the all-atom model 11 of the macromolecular chain which does not exist in reality. Accordingly, in the simulation method according to the present invention, the unit system in the molecular dynamics calculation performed using the coarse-grained model 6 can be converted into the unit system in the macromolecular chain which does not exist in reality. Thus, the simulation method according to the present invention is very useful in developing unknown macromolecular materials.

Process S8

In this process S8, using the virtual space 8 including the coarse-grained models 6 in the equilibrium state (FIG. 6), the deformation simulation of the macromolecular material is performed.

Such deformation calculation is continued until the amount of deformation becomes 1.0σ when, for example, the deformation velocity is 0.05 σ/τ. And the physical quantity such as stress due to the deformation of the virtual space 8 is computed.

Process S9

In this process S9, the physical quantity obtained in the above-mentioned deformation simulation is converted into that expressed in the unit system used in the macromolecular chain. In this process S9, based on the conversion rate obtained from the length, time or mass in the macromolecular chain and that in the coarse-grained model 6, the physical quantity (such as stress) in the virtual space 8 due to the deformation is converted into that expressed in the unit system used in the macromolecular chain.

In the simulation method in this embodiment, as a modification of the convert process S7, by converting the unit system in the coarse-grained model 6 into a plurality of unit systems in the macromolecular chain in the convert process S7, the physical quantity expressed in plural unit systems in the macromolecular chain can be obtained by making just one time the deformation simulation using the virtual space 8 including the coarse-grained models 6. Therefore, in the simulation method in this embodiment, it is possible to remarkably reduce the computational time of the deformation simulation.

Process S10

In this process S10, it is judged if the physical quantity obtained through the deformation simulation is within the allowable range.

If yes (within the allowable range), the process goes to the process S11.

If no (outside the allowable range), the conditions of the virtual space 8 and the coarse-grained models 6 are changed (process S12), Then, the processes S8 to S11 are repeated.

Process S11

In this process S11, based on the structure of the macromolecular chain and the conditions set to the coarse-grained models 6 and the virtual space 8, the macromolecular material is manufactured.

Therefore, in the simulation method in this embodiment, it is possible to efficiently design the macromolecular material having the physical quantity within the allowable range.

The invention claimed is:

1. A computer simulation method for a macromolecular material comprising the steps of:
    defining a coarse-grained model of a macromolecular chain modeled by a plurality of beads;
    performing a molecular dynamics calculation, using the coarse-grained model disposed in a predetermined virtual space;
    computing a Rouse parameter of the coarse-grained model;

defining an all-atom model of an arbitrary macromolecular chain modeled by a plurality of particle models of respective atoms;
performing a molecular dynamics calculation by the computer, using the all-atom model disposed in a predetermined virtual space;
computing a Rouse parameter of the all-atom model, wherein
the computing of a Rouse parameter of the all-atom model comprises obtaining the entire length of the all-atom model, and
the obtaining of the entire length of the all-atom model comprises
  a step in which the position of a carbon atom of the all-atom model at one end thereof is fixed relatively to the virtual space,
  a step in which a carbon atom of the all-atom model at the other end thereof is forced to move away from said one end, while performing the molecular dynamics calculation, so that the all-atom model is forcibly stretched,
  a step in which the forcibly stretched all-atom model is structurally stabilized by performing a calculation according to a molecular mechanics method, and
  a step in which the distance between said one end and other end of the all-atom model structurally stabilized is computed as the entire length Lf of the all-atom model;
converting a unit system employed in the molecular dynamics calculation performed by the use of the coarse-grained model into a unit system employed in the macromolecular chain, using the obtained Rouse parameter of the coarse-grained model and the obtained Rouse parameter of the all-atom model;
performing a deformation simulation of the macromolecular material, using a virtual space including the coarse-grained models, to obtain a physical quantity of the macromolecular material;
converting the obtained physical quantity into that expressed in the unit system employed in the macromolecular chain;
judging if the physical quantity is within an allowable range; and
if the physical quantity is outside the allowable range,
changing conditions set to the virtual space and the coarse-grained models based on which the deformation simulation is performed, and
repeating the performing of the deformation simulation, the converting of the physical quantity, and the judging of the physical quantity;
if the physical quantity is within the allowable range,
outputting the conditions set to the coarse-grained models and the virtual space and manufacturing the macromolecular material based thereon.

2. The method according to claim 1, wherein
the Rouse parameter of the coarse-grained model includes a length parameter $b_c$, a time parameter $\tau_c$, and a friction parameter $\zeta_c$,
the Rouse parameter of the all-atom model includes a length parameter $b_f$, a time parameter $\tau_f$, and a friction parameter $\zeta_f$,
in the step of converting the unit system, a unit length, a unit time, or a unit mass employed in the molecular dynamics calculation performed using the coarse-grained model is converted into a length, a time, or a mass in the macromolecular chain.

3. The method according to claim 2, wherein
the length parameter $b_c$ in the coarse-grained model is defined by the following expression (1)

$$b_c = \frac{\langle R_c^2 \rangle}{L_c} \quad \text{expression (1)}$$

$$L_c = A_c \times (N_c - 1)$$

wherein
$\langle R_c^2 \rangle$ is an ensemble average relating to a length $R_c$ of an end-to-end vector V1 of the coarse-grained model,
$L_c$ is the entire length of the coarse-grained model,
$A_c$ is an equilibrium length between the beads, and
$N_c$ is the number of the beads per one coarse-grained model.

4. The method according to claim 3, wherein
the time parameter $\tau_c$ in the coarse-grained model is defined as a time required for the value of a time correlation function of the end-to-end vector of the coarse-grained model to decrease to 1/e.

5. The method according to claim 3, wherein
the friction parameter $\zeta_c$ in the coarse-grained model is defined by the following expression (2),
$k_B$ is the Boltzmann's constant, and
T is the absolute temperature.

6. The method according to claim 3, wherein
the length parameter $b_f$ in the all-atom model is defined by the following expression (3), $$b_f = \frac{\langle R_f^2 \rangle}{L_f} \quad \text{expression (3)}$$

wherein
$\langle R_f^2 \rangle$ is an ensemble average relating to a length $R_f$ of an end-to-end vector V2 of the all-atom model, and
$L_f$ is the entire length of the all-atom model.

7. The method according to claim 3, wherein
the time parameter $\tau_f$ is defined as a time required for the value of a time correlation function of an end-to-end vector of the all-atom model to decrease to 1/e.

8. The method according to claim 3, wherein
the friction parameter $\zeta_f$ is defined by the following expression (4)

$$\zeta_f = \frac{3\pi^2 \times k_B \times T \times \tau_f}{N_f^2 \times b_f^2} \quad \text{expression (4)}$$

$$N_f = \frac{L_f}{b_f}$$

wherein
$b_f$ is the length parameter of the all-atom model,
$\tau_f$ is the time parameter of the all-atom model,
$N_f$ is the number of the particle models per one all-atom model,
$L_f$ is the entire length of the all-atom model,
$k_B$ is the Boltzmann's constant, and
T is the absolute temperature.

9. The method according to claim 2, wherein
the time parameter $\tau_c$ in the coarse-grained model is defined as a time required for the value of a time correlation function of an end-to-end vector of the coarse-grained model to decrease to 1/e.

10. The method according to claim 9, wherein
the friction parameter $\zeta_c$ in the coarse-grained model is defined by the following expression (2), $$\zeta_c = \frac{3\pi^2 \times k_B \times T \times \tau_c}{N_c^2 \times b_c^2} \quad \text{expression (2)}$$

wherein
$b_c$ is the length parameter of the coarse-grained model,
$\tau_c$ is the time parameter of the coarse-grained model,
$N_c$ is the number of the beads per one coarse-grained model, $$\zeta_f = \frac{3\pi^2 \times k_B \times T \times \tau_f}{N_f^2 \times b_f^2} \quad \text{expression (4)}$$

$$N_f = \frac{L_f}{b_f}$$

wherein
$b_f$ is the length parameter of the all-atom model,
$\tau_f$ is the time parameter of the all-atom model,
$N_f$ is the number of the particle models per one all-atom model,
$L_f$ is the entire length of the all-atom model,
$k_B$ is the Boltzmann's constant, and
T is the absolute temperature.

11. The method according to claim 9, wherein
the length parameter $b_f$ in the all-atom model is defined by the following expression (3), $$b_f = \frac{\langle R_f^2 \rangle}{L_f} \quad \text{expression (3)}$$

wherein
$\langle R_f^2 \rangle$ is an ensemble average relating to a length $R_f$ of an end-to-end vector V2 of the all-atom model, and
$L_f$ is the entire length of the all-atom model.

12. The method according to claim 9, wherein
the time parameter $\tau_f$ is defined as a time required for the value of a time correlation function of an end-to-end vector of the all-atom model to decrease to 1/e.

13. The method according to claim 9, wherein
the friction parameter $\zeta_f$ is defined by the following expression (4)

$$\zeta_c = \frac{3\pi^2 \times k_B \times T \times \tau_c}{N_c^2 \times b_c^2} \quad \text{expression (2)}$$

wherein
$b_c$ is the length parameter of the coarse-grained model,
$\tau_c$ is the time parameter of the coarse-grained model,
$N_c$ is the number of the beads per one coarse-grained model,
$k_B$ is the Boltzmann's constant, and
T is the absolute temperature.

14. The method according to claim 2, wherein
the friction parameter $\zeta_c$ in the coarse-grained model is defined by the following expression (2), $$\zeta_c = \frac{3\pi^2 \times k_B \times T \times \tau_c}{N_c^2 \times b_c^2} \quad \text{expression (2)}$$

wherein
$b_c$ is the length parameter of the coarse-grained model,
$\tau_c$ is the time parameter of the coarse-grained model,
$N_c$ is the number of the beads per one coarse-grained model,
$k_B$ is the Boltzmann's constant, and
T is the absolute temperature.

15. The method according to claim 14, wherein
the length parameter $b_f$ in the all-atom model is defined by the following expression (3), $$b_f = \frac{\langle R_f^2 \rangle}{L_f} \quad \text{expression (3)}$$

wherein
$\langle R_f^2 \rangle$ is an ensemble average relating to a length $R_f$ of an end-to-end vector V2 of the all-atom model, and
$L_f$ is the entire length of the all-atom model.

16. The method according to claim 14, wherein
the time parameter $\tau_f$ is defined as a time required for the value of a time correlation function of an end-to-end vector of the all-atom model to decrease to 1/e.

17. The method according to claim 2, wherein
the length parameter $b_f$ in the all-atom model is defined by the following expression (3), $$b_f = \frac{\langle R_f^2 \rangle}{L_f} \quad \text{expression (3)}$$

wherein
$\langle R_f^2 \rangle$ is an ensemble average relating to a length $R_f$ of an end-to-end vector V2 of the all-atom model, and
$L_f$ is the entire length of the all-atom model.

18. The method according to claim 17, wherein
the time parameter $\tau_f$ is defined as a time required for the value of a time correlation function of the end-to-end vector V2 of the all-atom model to decrease to 1/e.

19. The method according to claim 2, wherein
the time parameter $\tau_f$ is defined as a time required for the value of a time correlation function of an end-to-end vector of the all-atom model to decrease to 1/e.

20. The method according to claim 2, wherein
the friction parameter $\zeta_f$ is defined by the following expression (4)

$$\zeta_f = \frac{3\pi^2 \times k_B \times T \times \tau_f}{N_f^2 \times b_f^2} \quad \text{expression (4)}$$

$$N_f = \frac{L_f}{b_f}$$

wherein
$b_f$ is the length parameter of the all-atom model,
$\tau_f$ is the time parameter of the all-atom model, $N_f$ is the number of the particle models per one all-atom model,
$L_f$ is the entire length of the all-atom model,
$k_B$ is the Boltzmann's constant, and
T is the absolute temperature.

* * * * *